United States Patent [19]

Jamshidi

[11] Patent Number: 5,489,276
[45] Date of Patent: Feb. 6, 1996

[54] VACUUM TUBE TIP CONSTRUCTION

[75] Inventor: Khosrow Jamshidi, St. Paul, Minn.

[73] Assignee: KorMed, Inc., Edina, Minn.

[21] Appl. No.: 320,002

[22] Filed: Oct. 7, 1994

[51] Int. Cl.[6] .................................................. A61M 5/32
[52] U.S. Cl. ................................................. 604/268
[58] Field of Search ..................... 604/268, 239, 604/264, 272, 280, 266

[56] References Cited

U.S. PATENT DOCUMENTS 3,516,410  6/1970  Hakim ...................................... 604/268
4,068,664  1/1978  Sharp et al. ............................. 604/268

*Primary Examiner*—John D. Yasko
*Attorney, Agent, or Firm*—Nawrocki, Rooney & Sivertson

[57] ABSTRACT

A vacuum tube tip for use proximate loose tissue. The vacuum tube tip including an elongated tube having a longitudinal axis, a peripheral wall and a distal tip. At least one opening extends through the peripheral wall proximate the distal end. At least one fin is disposed proximate the opening. The fin is operably enacted to the peripheral wall of the tube and extends generally away from the tube. The fin is configured so that when a vacuum is created into the tube through the opening, loose tissue drawn toward the opening is held away from the opening by the fin.

4 Claims, 2 Drawing Sheets

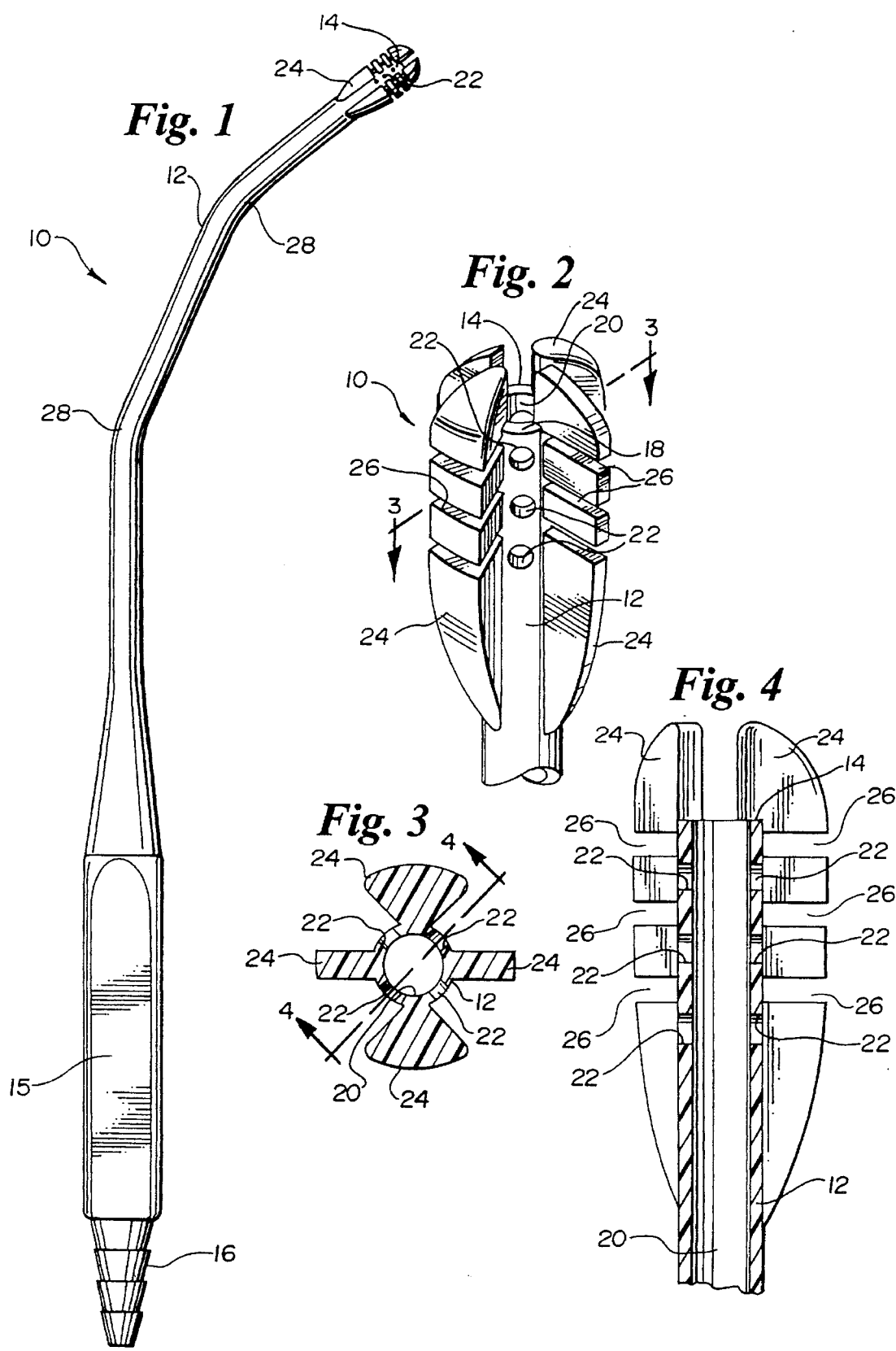

VACUUM TUBE TIP CONSTRUCTION

TECHNICAL FIELD

The present invention pertains generally to vacuum tube tips for vacuum tubes. Vacuum tubes and tips are often used in medical applications to aspirate blood and other liquids from body cavities during surgical or dental procedures. Aspiration of body cavities is often performed to enable surgeons or dentists to view and reach bodily structures within the cavities obscured by pooled liquids. Vacuum tubes can also be used generally for removing unwanted liquids or small solids.

BACKGROUND OF THE INVENTION

Vacuumtube tips usually include an elongated tube having a distal end. The tips are typically operably connected to a compressor which generates a vacuum creating a suction into an opening proximate the distal end of the tip.

Prior art tips typically have a single opening proximate their distal end. The opening is generally defined by a plane approximately perpendicular to the longitudinal axis of the elongated tube. In prior tips the cross-section of the opening was as large or larger than the cross-sectional area of the tube.

When prior tubes are used proximate loose bodily tissue, the suction into the tube, in addition to aspirating the body cavity, would draw the loose or flexible tissue toward the opening. The loose or flexible tissue might even be drawn into the opening, clogging the opening and preventing further aspiration from occurring. Thus, close attention had to be paid to the tip to prevent clogging of the opening with tissue.

SUMMARY OF THE INVENTION

The present invention is a vacuum tube tip for use proximate loose or flexible bodily tissue which could be drawn into the opening in the distal end of the tip. The invention provides the advantage of increasing the efficiency of aspirating liquids and small solids in proximate loose tissue. Improved efficiency is achieved by reducing clogging of the vacuum tube tip with loose tissue by providing an arrangement of additional openings and fins proximate the distal end of the tip.

The vacuum tube tip, for use proximate loose tissue, includes an elongated tube having a longitudinal axis, a peripheral wall and a distal end. There is at least one opening through the peripheral wall proximate the distal end. At least one fin is disposed proximate the opening. The fin is operably connected to the peripheral wall of the tube and extends generally away from the tube. The fin is configured so that when a vacuum is created into the tube through the opening, loose tissue drawn toward the opening is held away from the opening by the fin.

In one embodiment of the vacuum tube tip there are at least two radially spaced rows of openings proximate the distal end. Each row extends generally axially along the tube and includes at least two openings through the peripheral wall. At least one fin is disposed between each row. The fin is operably connected to the peripheral wall of the tube and extends generally away from the tube.

The fin may have one or more notches extending through the fin toward the tube. When a suction is created into the tube through the openings loose tissue drawn toward the openings is held away from the openings by the fins. Liquids and small solids are allowed to flow through the notches into the openings.

In one embodiment, the fin may extend axially approximately parallel each row of openings. Further, the fin may extend beyond the tube in the direction of the distal end and beyond the last opening in the opposite direction. The notches through the fin may be disposed axially on either side of the openings.

In an embodiment of the invention, the vacuum tube tip has at least one axial bend. In that embodiment, the rows of openings and the fins extend along the tube away from the distal end at least to the bend.

BRIEF DESCRIPTION OF THE DRAWINGS

FIG. 1 is a side elevational view of an embodiment of the vacuum tube tip in accordance with the present invention;

FIG. 2 is a perspective view of a plurality of fins and openings proximate the distal end of the vacuum tube tip shown in FIG. 1;

FIG. 3 is a cross-sectional view taken generally along line 3—3 of FIG. 2;

FIG. 4 is a cross-sectional view taken generally along line 4—4 of FIG. 3; and

DETAILED DESCRIPTION OF THE PREFERRED EMBODIMENT

Figure 5:
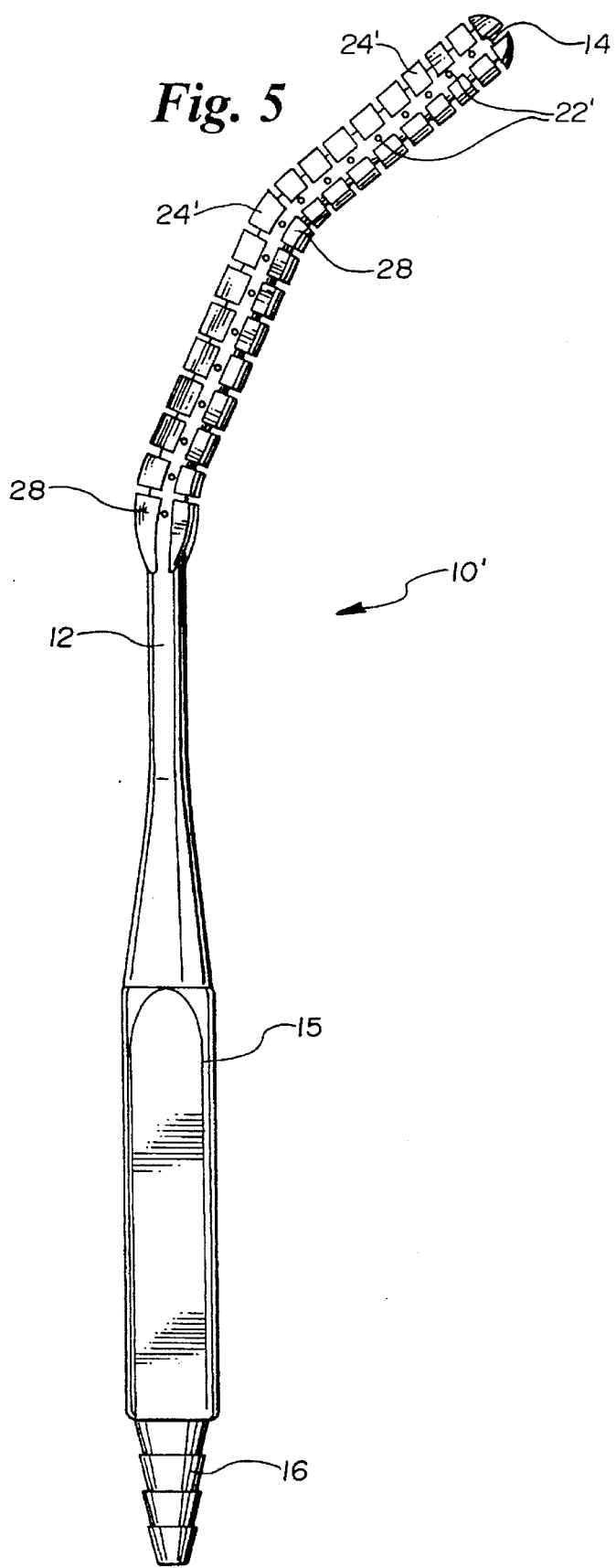
FIG. 5 is a view, similar to FIG. 1, showing an alternative embodiment of the vacuum tube tip.

Referring now to the drawings wherein like reference numerals designate like elements throughout the several views, FIG. 1 shows a vacuum tube tip 10 for use proximate loose tissue. As shown in FIG. 1, tip 10 includes an elongated tube 12 having a distal end 14 and a proximal end operably connected to a handle 15. Handle 15 is preferably equipped with a fixture 16 for operably connecting vacuum tube tip 10 to a compressor in a manner well known in the art.

FIG. 2 shows a portion of vacuum tube tip 10 proximate distal end 14. Tube 12 includes a preferably cylindrically shaped peripheral wall 18 surrounding a lumen 20. In the preferred embodiment lumen 20 is opened at distal end 14 of vacuum tube tip 10.

Disposed proximate distal end 14 is at least one opening 22 through the peripheral wall 18. In the preferred embodiment a plurality of openings 22 extend in at least one axially extending row of openings as shown in FIG. 2.

Vacuum tube tip 10 is for use proximate loose or flexible tissue which could be drawn into opening 22 proximate distal end 14 of tip 10. The invention provides the advantage of increasing the efficiency of aspirating liquids and small solids. The improved efficiency results from reducing clogging of the vacuum tube tip 10 with loose tissue.

Also disposed proximate distal end 14 is mean for holding loose tissue away from the openings. In the preferred embodiment means for holding loose tissue away from the openings includes at least one fin 24 proximate each row of openings 22. Fin 24 is operably connected to peripheral wall 18 of tube 12 and extends generally away from tube 12.

In one embodiment fin 24 has at least one notch 26 extending through fin 24 toward tube 12. Fin 24 preferably has a plurality of notches 26 as shown in FIG. 2.

FIG. 3 shows a cross-section through the portion of vacuum tube tip 10 proximate distal end 14 shown in FIG. 2. As shown FIG. 3, a plurality of openings 22 extending through peripheral wall 18 are radially spaced about tip 12. Preferably, each opening 22 shown in FIG. 3 is one opening 22 in each of four axially extending rows of openings 22.

As shown in FIG. 3, at least one fin 24 is disposed between each row of openings 22. Fins 24 preferably extend axially along peripheral wall 18 approximately parallel each row of openings 22. In one embodiment of the invention, at least one axially extending fin 24 has a generally wedged shaped cross-section lying in a plane approximately perpendicular to the longitudinal axis of tube 12. Fins 24 may also have a generally rectangular cross-section lying in a plane approximately perpendicular to the longitudinal axis of tube 12.

FIG. 4 shows a cross-section of vacuum tube tip 10 taken through tube 12 from the portion of vacuum tube tip 10 proximate distal end 14 shown in FIG. 3. As shown in FIG. 4, fins 24 preferably extend beyond tube 12 in the direction of distal end 14, and beyond the last opening 22 in the opposite direction. In the preferred embodiment, notches 26 are disposed axially on either side of openings 22.

FIG. 5 shows an alternative tip embodiment 10' of the vacuum tube tip shown in FIG. 1. Alternative embodiment 10' is essentially similar to embodiment 10 shown in FIG. 1. The rows of openings 22' and fins 24', however, extend axially along peripheral wall 18 further away from distal end 14 than openings 22 and fins 24 respectively of embodiment 10. As shown in FIG. 5, openings 22' are spaced further apart along tube 12 than are openings 22 of embodiment 10.

As shown in both FIGS. 5 and 1 tube 12 may have one or more axial bends 28. Openings 22' may be larger than openings 22. Fins 24' may be larger than fins 24 but otherwise are preferably configured similarly. Openings 22' and fins 24' preferably extend at least to the bend nearest distal end 14.

In use, proximal end fixture 16 of vacuum tube tip 10 or alternate embodiment 10' is operably connected to a compressor in a manner well known in the art. A user can hold vacuum tube tip 10 or 10' and direct distal end 14 to a portion of a body cavity where aspiration is necessary. Bends 28 in tube 12 enable the user to guide tube 12 and distal end 14 into the desired location within the body cavity.

The portion of tube 12 having openings 22 or 22' is placed in the fluid to be aspirated. A vacuum created by the compressor creates a suction into openings 22 or 22' and the open distal end 14. Fluids and/or relatively small solids are drawn into openings 22 or 22' and open distal end 14, aspirating the body cavity.

While aspirating the body cavity, loosely or flexibly connected tissues proximate openings 22 or 22' and the open distal end 14 of tube 12 are drawn towards these openings. Fins 24 or 24' extend away from peripheral wall 18 to hold the tissue away from these openings.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A vacuum tube tip for use proximate loose tissue, comprising:

an elongated tube having a longitudinal axis, a peripheral wall, and a distal end;

a plurality of openings through the peripheral wall of the tube proximate the distal end thereof, said openings being spaced circumferentially about the tube and axially along the tube to form at least two circumferentially-spaced, axially extending rows; and a plurality of fins disposed proximate the openings, each fin extending outwardly from the peripheral wall of the tube with at least one fin being disposed circumferentially between adjacent openings, each fin extending generally axially and generally parallel to the longitudinal axis of the elongated tube, at least one of the axially extending fins having a generally wedge-shaped cross-section defining a plane generally perpendicular to the longitudinal axis of the elongated tube.

2. A vacuum tube tip for use proximate loose tissue, comprising:

an elongated tube having a longitudinal axis, a peripheral wall, and a distal end;

a plurality of openings through the peripheral wall of the tube proximate the distal end thereof, said openings being spaced circumferentially about the tube and axially along the tube to form at least two circumferentially-spaced, axially extending rows; and a plurality of fins disposed proximate the openings, each fin extending outwardly from the peripheral wall of the tube with at least one fin being disposed circumferentially between adjacent openings, each fin extending generally axially and generally parallel to the longitudinal axis of the elongated tube, at least one of the axially extending fins having a generally rectangular cross-section defining a plane generally perpendicular to the longitudinal axis of the elongated tube.

3. A vacuum tube tip for use proximate loose tissue, comprising:

an elongated tube having a longitudinal axis, a peripheral wall, and a distal end;

at least two circumferentially-spaced rows of openings proximate the distal end of the tube, each row extending generally axially along the tube; and at least one fin disposed between adjacent rows, the fin extending outwardly from the peripheral wall of the tube and having at least one notch extending through the fin toward the tube so that, when a vacuum is created within the tube through the openings, loose tissue drawn toward the openings is held away from the openings by the fins and fluids are allowed to flow through the notch, said at least one fin extending generally axially and generally parallel to the longitudinal axis of the elongated tube, wherein at least one of the axially extending fins has a generally wedge-shaped cross-section defining a plane generally perpendicular to the longitudinal axis of the elongated tube.

4. A vacuum tube tip for use proximate loose tissue, comprising:

an elongated tube having a longitudinal axis, a peripheral wall, and a distal end;

at least two circumferentially-spaced rows of openings proximate the distal end of the tube, each row extending generally axially along the tube; and at least one fin disposed between adjacent rows, the fin extending outwardly from the peripheral wall of the tube and having at least one notch extending through the fin toward the tube so that, when a vacuum is created within the tube through the openings, loose tissue drawn toward the openings is held away from the openings by the fins and fluids are allowed to flow through the notch, said at least one fin extending generally axially and generally parallel to the longitudinal axis of the elongated tube, wherein at least one of the axially extending fins has a generally rectangular cross-section defining a plane generally perpendicular to the longitudinal axis of the elongated tube.

* * * * *